(12) United States Patent
Moeller et al.

(10) Patent No.: US 7,507,837 B2
(45) Date of Patent: *Mar. 24, 2009

(54) PROCESS FOR PERFORMING AN ISOLATED PD(II)-MEDIATED OXIDATION REACTION

(75) Inventors: Kevin D. Moeller, Overland, MO (US); Eden Tesfu, St. Louis, MO (US); Karl Maurer, Everett, WA (US)

(73) Assignee: CombiMatrix Corporation, Mukilteo, WA (US)

( * ) Notice: Subject to any disclaimer, the term of this patent is extended or adjusted under 35 U.S.C. 154(b) by 303 days.

This patent is subject to a terminal disclaimer.

(21) Appl. No.: 11/295,847

(22) Filed: Dec. 7, 2005

(65) Prior Publication Data

US 2006/0205959 A1 Sep. 14, 2006

Related U.S. Application Data

(63) Continuation-in-part of application No. 11/063,402, filed on Feb. 22, 2005.

(51) Int. Cl.
*C07D 311/08* (2006.01)
(52) U.S. Cl. .................................. 549/289
(58) Field of Classification Search .......... 549/289
See application file for complete search history.

(56) References Cited

U.S. PATENT DOCUMENTS 6,093,302 A * 7/2000 Montgomery ............... 205/122
2006/0151335 A1 * 7/2006 Tian et al. .................... 205/488
2006/0189166 A1 * 8/2006 Tesfu et al. .................. 438/789
2008/0039342 A1 * 2/2008 Tian et al. .................... 506/13

* cited by examiner

*Primary Examiner*—Taofiq A Solola
(74) *Attorney, Agent, or Firm*—Michael D. Vrbanac

(57) ABSTRACT

There is disclosed a process for performing an isolated Pd(II) mediated oxidation reaction electrochemically. The inventive process is performed on an electrode array device having a plurality of separately addressable electrodes. Preferably, the Pd(II) mediated oxidation is a Wacker reaction. Specifically, there is disclosed a process for conducting an isolated Pd(II) mediated oxidation on a plurality of electrodes, comprising providing an electrode array device having a plurality of electrodes with a conductive electrode surface and a matrix or coating material over the electrodes surfaces; providing a solution bathing the electrode array matrix or coating material and electrode surfaces, wherein the solution comprises a transition metal species and a confining agent; and biasing one or a plurality of electrodes ("selected electrode or electrodes") with a voltage or current to regenerate the transition metal species required for the isolated Pd(II) mediated oxidation, whereby the confining agent limits diffusion of the transition metal species to a volume surrounding each selected electrode surface.

6 Claims, 16 Drawing Sheets

Figure 1: Selective Pd(II) oxidation on a chip.
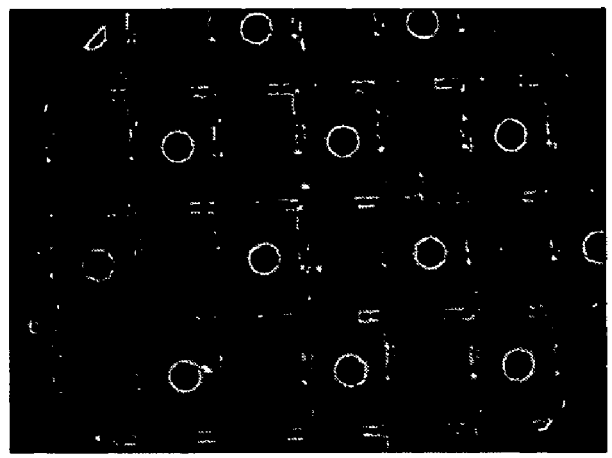
Figure 2
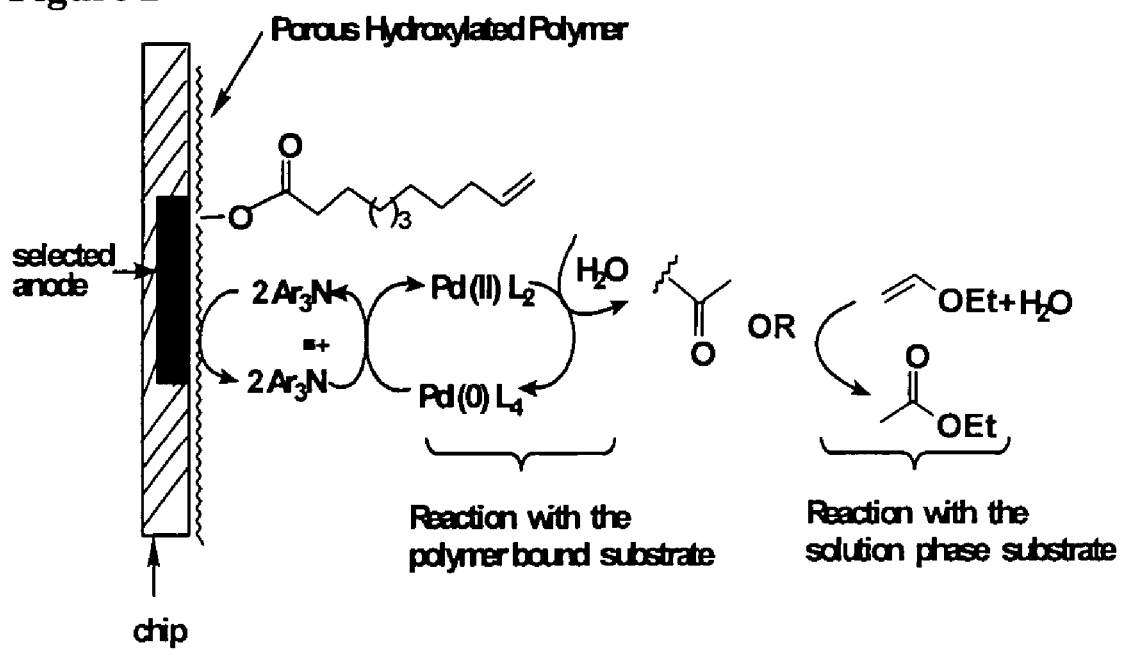

Figure 9
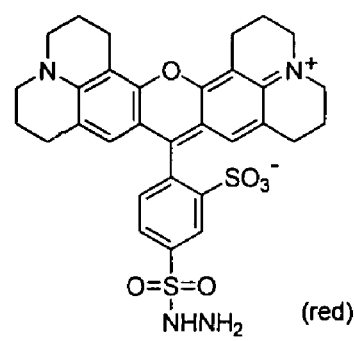 (red)  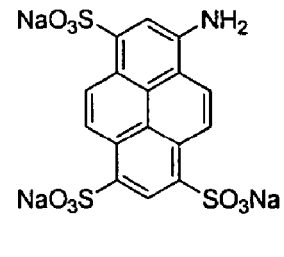 (green)

1

PROCESS FOR PERFORMING AN ISOLATED PD(II)-MEDIATED OXIDATION REACTION

CROSS-REFERENCE TO RELATED APPLICATION

This patent application is a continuation-in-part of U.S. patent application Ser. No. 11/063,402 filed 22 Feb. 2005.

TECHNICAL FIELD OF THE INVENTION

The present invention provides a process for performing an isolated Pd(II) mediated oxidation reaction electrochemically. The inventive process is also performed on an electrode array device having a plurality of separately addressable electrodes. Preferably, the Pd(II) mediated oxidation is a Wacker reaction. Specifically, the inventive process provides a process for conducting an isolated Pd(II) mediated oxidation on a plurality of electrodes, comprising providing an electrode array device having a plurality of electrodes with a conductive electrode surface and a matrix or coating material over the electrodes surfaces; providing a solution bathing the electrode array matrix or coating material and electrode surfaces, wherein the solution comprises a transition metal species and a confining agent; and biasing one or a plurality of electrodes ("selected electrode or electrodes") with a voltage or current to regenerate the transition metal species required for the isolated Pd(II) mediated oxidation, whereby the confining agent limits diffusion of the transition metal species to a volume surrounding each selected electrode surface.

BACKGROUND OF THE INVENTION

Electronically addressable chip-based molecular libraries (Lipshutz et al., Nature Genetics, 21:20, 1999; Pirrung, Chem. Rev. 97:473, 1997; Webb et al., J. Steroid Biochem. Mol. Biology, 85:183, 2003; Shih et al., J. Virological Methods, 111:55, 2003) have long been desired but have not been created. CombiMatrix Corporation scientists have been utilizing active-semiconductor electrode arrays that incorporate individually addressable microelectrodes to synthesize oligonucleotide and polypeptide molecules (U.S. Pat. No. 6,093,302; WO/0053625; Oleinikov et al., J. Proteome Res., 2:313, 2003; Sullivan et al., Anal. Chem., 71:369, 1999; Zhang et al., Anal. Chim. Acta, 421:175, 2000; and Hintsche et al., Electroanal. 12:660, 2000).

In this way, each unique set of molecules in a library can be located proximal to a selected electrode or set of electrodes that can, in turn, be used to monitor their behavior (Dill et al., Analytica Chimica Acta, 444:69, 2001). This is accomplished by coating the electrode-containing array devices with a porous polymer and then utilizing the electrodes to both attach monomers to the electrode array devices and then generate reagents capable of performing reactions on the monomers.

Pd(II) mediated oxidations are powerful synthetic tools that allow for the selective functionalization of organic molecules. Therefore, there is a need in the art for a combinatorial chemical synthesis device that could perform Pd(II) mediated oxidations on an electrode array. In particular, to perform a Pd(II) mediated oxidation on a selected electrode on the device. As a proof of principle, a Wacker oxidation (conversion of an alkene to a ketone) was used for this purpose. Such a device and process would expand the number of different molecules that could be constructed. Such a tool would allow for massively parallel electrochemical synthesis in small volumes on an electrode array device and create arrays containing highly diverse libraries of chemical compounds that are different from each other yet synthesized in parallel. Such "combinatorial libraries" could be synthesized rapidly, in small volumes and with high diversity.

Therefore, there is a need in the art to be able to perform rapid and diverse synthesis of chemical libraries on an electrode array device for large scale screening of combinatorial libraries. The present invention was made to address this need in the art.

SUMMARY OF THE INVENTION

The present invention provides a process for conducting an isolated Pd(II) mediated reaction on a plurality of electrodes, comprising:

(a) providing an electrode array device having a plurality of metallic or conductive electrodes each with a conductive surface, and having a matrix or coating material over the electrodes surfaces;

(b) providing a solution bathing the electrode array device, wherein the solution comprises a transition metal species and a confining agent; and (c) biasing one or a plurality of electrodes (selected electrode or electrodes) on the electrode array device with a voltage or current to regenerate the transition metal species consumed during the Pd(II)-mediated reaction, whereby the confining agent limits diffusion of the transition metal species to a volume surrounding each selected electrode surface.

Preferably, the isolated Pd(II) mediated oxidation is selected from the group consisting of a Wacker reaction, a Saegusa reaction, oxidative aryl coupling reactions, alkene to π-allyl palladium conversions, enol ether—organometallic coupling reactions, and any other stoichiometric Pd(II) oxidation (for a summary see: "Chapter 3. Oxidative Reactions with Pd(II) Compounds" in Palladium Reagents and Catalysts, Tsuji, J.; John Wiley and Sons; West Sussex, England; 1995, pp 19-108).

Preferably, the transition metal is a Pd (II) containing species. Most preferably, the transition metal is $Pd(OAc)_2$. Preferably, the Pd(II) species is generated by oxidation from Pd(0) by an intermediate oxidant generated by a regeneration reaction at a selected electrode. Most preferably, the intermediate oxidant species is a triarylamine cation radical generated from a triaryl amine at the electrode. Preferably, the confining agent is a reductant added to the solution sufficient to convert Pd(II) back to Pd(0) in areas not proximal to an activated electrode. Most preferably, the confining agent is a reductant selected from the group consisting of substituted or an unsubstituted alkyl vinyl ethers, divinyl ether, aryl vinyl ether, alkene, $H_2$, hydroquinones, and combinations thereof. More preferably, the confining agent is a substituted or unsubstituted vinyl alkyl ether, wherein the alkyl moiety is a $C_{1-8}$ alkyl group. Preferably, the biasing step uses a voltage no greater than 5V. Preferably, the biasing step was performed for a time of from about 1 sec to about 10 min using a pulsed voltage or nonpulsed voltage.

The present invention further provides a method for building addressable libraries on an electrode array The present invention further provides a process for synthesizing site-selective coumarins at known locations of an electrode array device, comprising:

(a) providing an electrode array device with a coating of the at least the region above the electrodes with a porous polymer matrix having free amine groups;

(b) coupling a phenol substrate at selected electrodes of the electrode array device to form a bound phenol substrate; and (c) performing a site selected Pd(II) catalysed cyclooxidation reaction at selected electrode sites by providing a solution bathing the electrode array device, wherein the solution comprises a transition metal species and a confining agent, Preferably, the cyclooxidation reaction further comprises biasing one or a plurality of selected electrodes on the electrode array device with a voltage or current to regenerate the transition metal species consumed during the cyclooxidation reaction. Preferably, the porous polymer matrix having free amine groups is selected from the group consisting of amidited agarose, sucrose having oligonucleotide moieties each having an amino-modifier, and combinations thereof. Preferably, an amino modifier is selected from the group consisting of 5'-3-aminopropyloxy, 2-aminoethoxy, 2(2-aminoethoxy)ethoxy, 2(2(2aminoethoxy)ethoxy)ethoxy, 6-amino, and combinations thereof. Preferably, the phenol substrate is selected from the group consisting of 2-,3-,4-, or 5-substituted amino phenols, and combinations thereof, wherein the substitution is selected from the group consisting of $C_{1-6}$ alkyl, $C_{1-6}$ alkoxy, Cl, F, Br, hydroxy, amino$C_{1-6}$ alkyl, and amino.

The present invention further provides a process for site-selective oxidation of alcohols on an electrode array device, comprising:

(a) providing an electrode array device with a coating of at least the region above the electrodes with a porous polyhydroxylated polymer matrix;

(b) performing an oxidation reaction at selected electrode sites by providing a solution bathing the electrode array device, wherein the solution comprises a transition metal species;

(c) coupling an amine substrate at selected electrodes of the electrode array device to form a bound substrate.

Preferably, the oxidation reaction further comprises biasing one or a plurality of selected electrodes on the electrode array device with a voltage or current to regenerate the transition metal species consumed during the oxidation reaction. Preferably, the porous polyhydroxylated polymer matrix is composed of a material selected from the group consisting of agarose, dextrose, PEG, dextran, polyvinylalcohol, porous crosslinked polystyrene, poly(2 hydroxyethylacrylate), poly(hydroxylpropylacrylate), and combinations thereof.

BRIEF DESCRIPTION OF THE DRAWINGS

FIG. 1. Shows a picture of an array produced in the experiment of example #1, the bright spots are locations which were oxidized via the Wacker reaction and stained as specified, the dark spots are electrodes that were not utilized for the oxidation (the Pt electrodes block the background fluorescent originating from the chip itself).

FIG. 2 shows a schematic of the Wacker reaction as preformed in example 1.

FIG. 9 shows the structure of two fluorophore labeled amines for use in the reductive amination reactions.

FIG. 13 shows three reaction schemes.

DETAILED DESCRIPTION OF THE INVENTION

Figure 3:
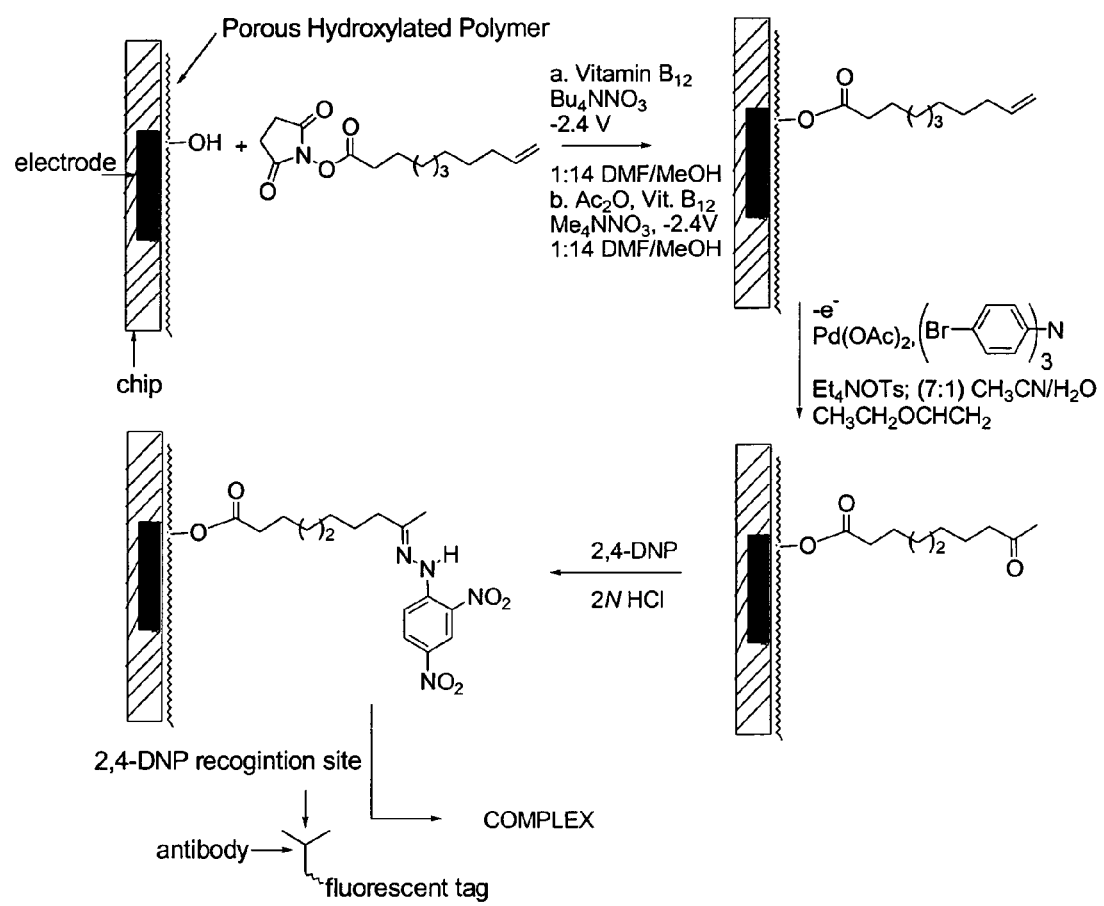
FIG. 3 shows the experimental procedure used in example 1.

In the exemplified experiments Pd(0) was oxidized to Pd(II) at selected electrodes on the electrode array device. Further, a confining agent was necessary to confine the reaction to the region surrounding a selected electrode, to preserve the fidelity of the combinatorial reaction scheme (that is, confining the reaction to the region in the porous matrix above the selected electrode and not to a neighboring unselected electrode). Ethyl vinyl ether was a preferred confining agent. This is because the reaction performed without the preferred confining agent, ethyl vinyl ether, led to significant spreading of signal away from selected electrode sites.

Additionally, since the Wacker reaction allows the generation of a ketone or an aldehyde (or a mixture of both) at a selective location this selectively produced ketone can be used to selectively immobilize an amine moiety on a biological molecule. ("Immobilization of Enzymes and Cells" by Bickerstaff 1997 Humana Press; and Pierce applications handbook 2003 p 137). Therefore, the present invention further provides a process for selectively immobilizing a biological molecule having a free amine moiety onto a selected region of a porous matrix, comprising:

(a) providing an electrode array device having a plurality of metallic or conductive electrodes each with a conductive surface;

(b) providing a solution bathing the electrode array device, wherein the solution comprises a Pd(II) metal species and a confining agent;

(c) biasing one or a plurality of selected electrodes on the electrode array device with a voltage or current to perform a reaction generating the Pd metal species consumed during the reaction and generating a free ketone or a free aldehyde moiety or a mixture of both, whereby the confining agent limits diffusion of the transition metal species to a volume surrounding each selected electrode surface; and (d) providing a biological material having a free amino moiety to the electrode array device to selectively immobilize to the porous matrix located adjacent to the selected electrode (s).

Preferably, the Pd(II) species is generated by oxidation from Pd(0) by an intermediate oxidant generated by a regeneration reaction at a selected electrode. Most preferably the intermediate oxidant species is a triarylamine cation radical generated from a triaryl amine at the electrode. Preferably, the confining agent is a reductant added to the solution sufficient to convert Pd(II) back to Pd(0) in areas not proximal to an activated electrode. Most preferably, the confining agent is a reductant selected from the group consisting of substituted or unsubstituted alkyl vinyl ethers, divinyl ether, aryl vinyl ether, alkene, $H_2$, hydroquinones, and combinations thereof. More preferably, the confining agent is a substituted or unsubstituted alkyl vinyl ether, wherein the alkyl moiety is a $C_{1-8}$ alkyl group. Preferably, the biasing step uses a voltage no greater than 5V. Preferably, the biasing step was performed for a time of from about 1 sec to about 10 min using a pulsed voltage or nonpulsed voltage.

The reagents generated at any given electrode were confined to the area surrounding the electrode. The confinement was accomplished by placing a substrate in the solution bathing the electrode array surface. The substrate "consumed" the reagent. For example, substrates that "consume" reagents include acids that consume bases, bases that consume acids, Pd(II) consumed with ethyl vinyl ether, allyl alkyl carbonate consuming Pd(0) and the like. Briefly, this process was described in connection with the generation of acids and bases confined to a volume on electrode array devices (see, for example, Montgomery U.S. Pat. No. 6,093,302, the disclosure of which is incorporated by reference herein). In other work, generation of a Pd(0) reagent was confined to the area proximal to the active electrode (patent application submitted).

The present invention was motivated by the desire to determine if the electrodes on an electrode array device could be used as anodes in the oxidation of Pd(0) to Pd(II) in order to use Pd(II) as a reagent at pre-selected sites on an electrode array device having a plurality of electrode sites (each separately addressable). The problem solved by the present invention was to find an efficient confinement strategy for the Pd(II) reagent generated so that it was confined to one electrode and did not cause a reaction at a neighboring electrode. This is necessary in order to be able to perform a transformation at one site without causing cross contamination with materials produced in other locations of the array.

In the case of Pd(0), Pd(0) was used to catalyze a reaction between an aryl iodide and an acrylate ester. Hence, most of the reagent generated at a selected electrode on an electrode array was not consumed by the reaction. Methyl allyl carbonate was used as a confining agent to react with any Pd(0) reagent leaving the vicinity of the active electrodes there by preventing its catalyzing the reaction in undesired location. (*Process for Performing an Isolated Heck Reaction Electrochemicaly on an Electrode Array Device* patent applied for Jan. 7, 2005 the disclosure of which is incorporated by reference herein).

In a preferred embodiment of the Pd(II) case, (for example a Wacker oxidation) the reagent which is generated is a Pd(II) species which is reduced to Pd(0) during the reaction process and is recycled by triarylamine radical cation generated at the electrode. The confining agent (ethyl vinyl ether) reacts with any Pd(II) reagent leaving the vicinity of the electrode, reducing it to Pd(0) which does not perform the Wacker oxidation (conversion of an alkene to a carbonyl compound), thereby preventing unwanted reaction at unactivated locations.

The present invention provides a process for conducting a parallel Wacker reaction on a plurality of electrodes, comprising (a) providing an electrode array device having a matrix or coating material over metallic or conductive electrodes surfaces and a plurality of electrodes;

(b) providing a solution bathing the electrode array device, wherein the solution comprises a transition metal species, solvent, and a confining agent; and (c) biasing one or a plurality of electrodes on the electrode array device with a voltage or current to regenerate the transition metal species consumed during the Wacker reaction, whereby the confining agent limits diffusion of the transition metal species to a volume surrounding each selected electrode surface.

The present invention further provides a process for conducting an isolated Pd(II) mediated reaction on a plurality of electrodes, comprising:

(a) providing an electrode array device having a matrix or coating material over metallic or conductive electrodes surfaces and a plurality of electrodes;

(b) providing a solution bathing the electrode array device, wherein the solution comprises a transition metal species, solvent, and a confining agent;

(c) biasing one or a plurality of electrodes on the electrode array device with a voltage or current to regenerate the transition metal species consumed during the Pd(II) mediated reaction, whereby the confining agent limits diffusion of the transition metal species to a volume surrounding each selected electrode surface.

Preferably, the isolated Pd(II) mediated oxidation is selected from the group consisting of a Wacker reaction, a Saegusa reaction, oxidative aryl coupling reactions, alkene to π-allyl palladium conversions, enol ether—organometallic coupling reactions, and any other stoichiometric Pd(II) oxidation (for a summary see: "Chapter 3. Oxidative Reactions with Pd(II) Compounds" in *Palladium Reagents and Catalysts*, Tsuji, J.; John Wiley and Sons; West Sussex, England; 1995, pp 19-108). Preferably, a Pd (II) species is stabilized with ligands. Preferably, the confining agent is an reductant added to solution sufficient to convert Pd(II) back to Pd(0) in areas not near to an active electrode. Most preferably, the confining agent is a reductant selected from the group consisting of substituted or unsubstituted alkyl vinyl ether, divinyl ether, aryl vinyl ether, alkene, $H_2$, hydroquinone, and combinations thereof. More preferably, the confining agent is a substituted or unsubstituted alkyl vinyl ether wherein the alkyl moiety can be a $C_{1-8}$ alkyl group. Preferably, the biasing step used a voltage no greater than 5 V. Preferably, the biasing step was performed for a time of from about 1 sec to 10 min.

Preferably, the transition metal reagent for the Wacker reaction is a $Pd(OAc)_2$.

The term "substituted" or "substitution," in the context of a moiety of the confining agent, means a moiety independently selected from the group consisting of (1) the replacement of a hydrogen on at least one carbon by a monovalent radical, (2) the replacement of two hydrogens on at least one carbon by a divalent radical, (3) the replacement of three hydrogens on at least one terminal carbon (methyl group) by a trivalent radical, (4) the replacement of at least one carbon and the associated hydrogens (e.g., methylene group) by a divalent, trivalent, or tetravalent radical, and (5) combinations thereof. Meeting valence requirements restricts substitution. Substitution occurs on alkyl, alkenyl, alkynyl, cycloalkyl, cycloalkenyl, cycloalkynyl, aryl, heterocyclic ring, and polycyclic groups, providing substituted alkyl, substituted alkenyl, substituted alkynyl, substituted cycloalkyl, substituted cycloalkenyl, substituted cycloalkynyl, substituted aryl group, substituted heterocyclic ring, and substituted polycyclic groups.

The groups that are substituted on an alkyl, alkenyl, alkynyl, cycloalkyl, cycloalkenyl, cycloalkynyl, aryl, heterocyclic ring, and polycyclic groups are independently selected from the group consisting of alkyl, alkenyl, alkynyl, cycloalkyl, cycloalkenyl, cycloalkynyl, aryl, heterocyclic ring, polycyclic group, halo, heteroatom group, oxy, oxo, carbonyl, amide, alkoxy, acyl, acyloxy, oxycarbonyl, acyloxycarbonyl, alkoxycarbonyloxy, carboxy, imino, amino, secondary amino, tertiary amino, hydrazi, hydrazino, hydrazono, hydroxyimino, azido, azoxy, alkazoxy, cyano, isocyano, cyanato, isocyanato, thiocyanato, fulminato, isothiocyanato, isoselenocyanato, selenocyanato, carboxyamido, acylimino, nitroso, aminooxy, carboximidoyl, hydrazonoyl, oxime, acylhydrazino, amidino, sulfide, thiol, sulfoxide, thiosulfoxide, sulfone, thiosulfone, sulfate, thiosulfate, hydroxyl, formyl, hydroxyperoxy, hydroperoxy, peroxy acid, carbamoyl, trimethyl silyl, nitrilo, nitro, aci-nitro, nitroso, semicarbazono, oxamoyl, pentazolyl, seleno, thiooxi, sulfamoyl, sulfenamoyl, sulfeno, sulfinamoyl, sulfino, sulfinyl, sulfo, sulfoamino, sulfonato, sulfonyl, sulfonyldioxy, hydrothiol, tetrazolyl, thiocarbamoyl, thiocarbazono, thiocarbodiazono, thiocarbonohydrazido, thiocarbonyl, thiocarboxy, thiocyanato, thioformyl, thioacyl, thiosemicarbazido, thiosulfino, thiosulfo, thioureido, thioxo, triazano, triazeno, triazinyl, trithio, trithiosulfo, sulfinimidic acid, sulfonimidic acid, sulfinohydrazonic acid, sulfonohydrazonic acid, sulfinohydroximic acid, sulfonohydroximic acid, and phosphoric acid ester, and combinations thereof.

As an example of a substitution, replacement of one hydrogen or ethane by a hydroxyl provides ethanol, and replacement of two hydogens by an oxo on the middle carbon of propane provides acetone (dimethyl ketone.) As a further example, replacement the middle carbon (the methenyl group) of propane by the oxy radical (—O—) provides dimethyl ether ($CH_3$—O—$CH_3$.) As a futher example, replacement of one hydrogen on a benzene by a phenyl group provides biphenyl. As provided above, heteroatom groups can be substituted inside an alkyl, alkenyl, or alkylnyl group for a methylene group (:$CH_2$) thus forming a linear or branched substituted structure rather than a ring or can be substituted for a methylene inside of a cycloalkyl, cycloalkenyl, or cycloalkynyl ring thus forming a heterocyclic ring. As a further example, nitrilo (—N═) can be substituted on benzene for one of the carbons and associated hydrogen to provide pyridine, or and oxy radical can be substituted to provide pyran.

The term "unsubstituted" means that no hydrogen or carbon has been replaced on an alkyl, alkenyl, alkynyl, cycloalkyl, cycloalkenyl, cycloalkynyl, or aryl group.

The following example supports the conclusion that a reaction (that is a preferred Pd(II) mediated reaction) has been performed at pre-selected sites on an electrochemically-addressable electrode array device. The experiment highlights the utility of a Pd(II) reagent on the electrode array device, and for the first time demonstrates the potential for employing a Pd(II) reagent to selectively construct molecules proximal to specific addressable electrodes.

Coumarin

Coumarins were synthesized proximal to the electrodes of an addressable electrode array device. This was accomplished via a Pd(II)-mediated coumarin formation or cycloaddition (Oyamada et al., *Chemistry Lett.* 380, 2002) proximal to the electrode surface. The ability of the electrode array device to signal a binding event was determined by treating the electrode array device with commercially available, coumarin-specific antibodies. These antibodies bound to the porous matrix proximal to the electrode surface that specifically contained the synthesized coumarins. When a ferrocene/ferroconium cation mixture was added, a cyclic voltammogram varied when antibody was bound, as the current between cathode and anode was lowered. It would appear that a blocking agent added across the coumarin layer inhibits electron transport. It provided a passivity layer not experienced by the other electrodes.

Figure 5:
FIG. 5 shows a fluorescent microscope image of an electrode array surface containing synthesized courmarin in a checkerboard pattern. Bound coumarin was recognized by anti-coumarin antibodies tagged with Texas Red (a fluorescent probe).

The coumarin synthesis began by coupling a phenol substrate ((1-methylamino)methyl 2,6-dimethoxy-4-hydroxybenzene or N-methyl, 2,6-dimethoxy-4-hydroxy-benzylamine) to the surface of the electrode array device via a urea linkageusing an amine based porous polymer. The phenol was placed on the entire surface of the electrode array device. The coumarin synthesis process took advantage of a Pd(II) catalyzed cycloaddition between the phenol substrate and an acetylene in the solution above the chips surface as describe previously utilizing the same chemistry developed for the Wacker oxidation, as described herein. The coumarin tagged electrode surface is shown in FIG. 5.

Figure 6:
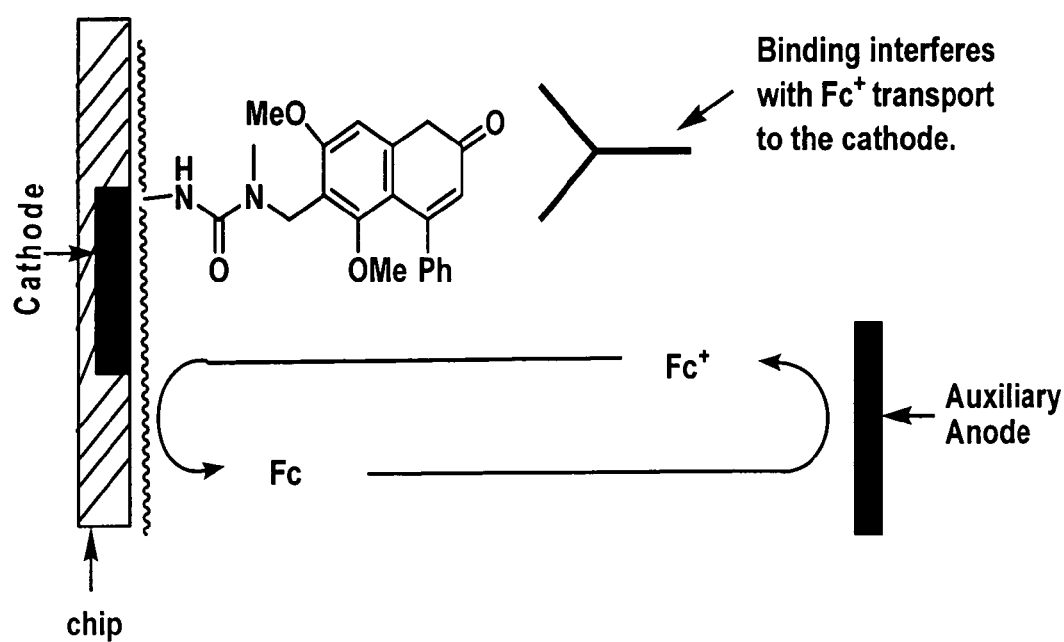
FIG. 6 shows a schematic of a redox cycle used for the detection of synthesized coumarin and bound antibodies.

The synthesis of coumarin was confined to specific electrodes, as determined by anti-coumarin antibodies containing a fluorophore. This was accomplished by incubating the synthesized electrode array device with biotinylated anti-coumarin antibody followed by incubation with a Texas red conjugated streptavidin. FIG. 6 shows a fluorescent microscope image of a electrode array device where a checkerboard pattern of electrodes was used as anodes.

The confinement strategy was effective. The flourescent markers showed that coumarin was synthesized only proximal to the electrodes where Pd(II) was produced.

Signaling

Figure 7:
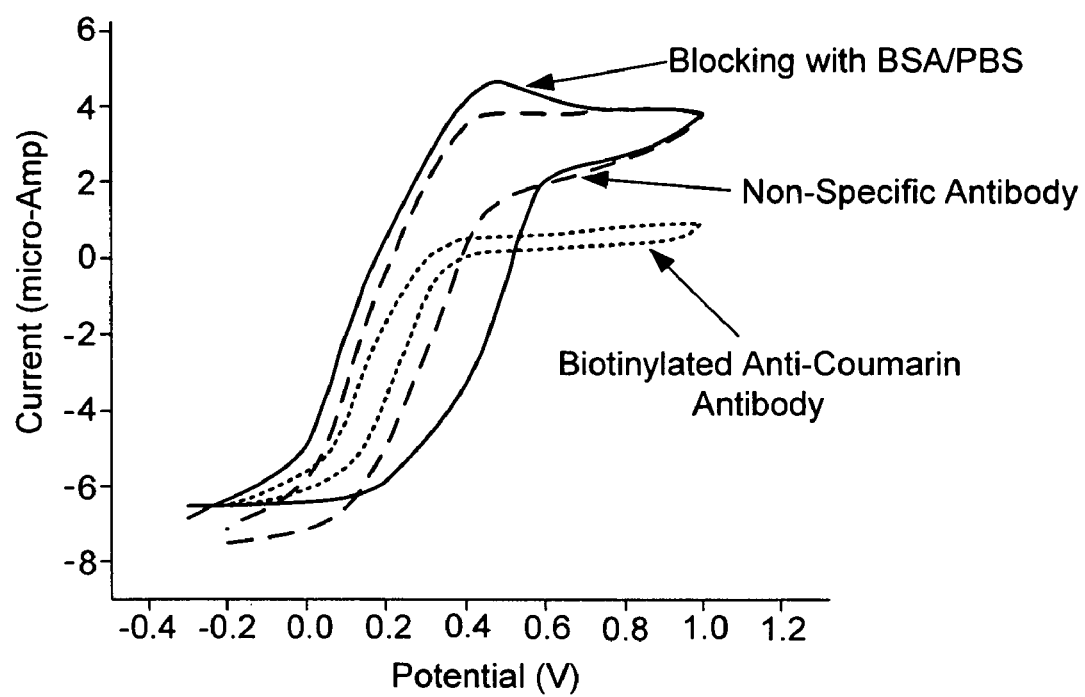
FIG. 7 shows cyclic voltammetry curves for couamrin synthesized electrodes using a ferrocene/ferrocinium couple: The electrode array incubated with BSA, non-specific antibdoy and coumarin specific antibody.

An electrode array device having 12,544 electrodes/$cm^2$ was utilized. Of the approximately 12,000 electrodes, a block of 121 electrodes were employed as anodes for coumarin synthesis. The electrode array device was submerged in a reaction solution containing a ferrocene/ferrocinium cation redox couple. This electrochemical cycle is illustrated in FIG. 7.

Cyclic voltammetry (CV) was used to assay the formation of coumarin on the electrode. The electrodes were then used in parallel as one working electrode in a two-electrode electrochemical cell with indium tin oxide acting as the counter electrode. The electrolyte solution was 2×PBST with a redox couple of ferrocene acetic acid/ferrocinium acetic acid cation.

Figure 4:
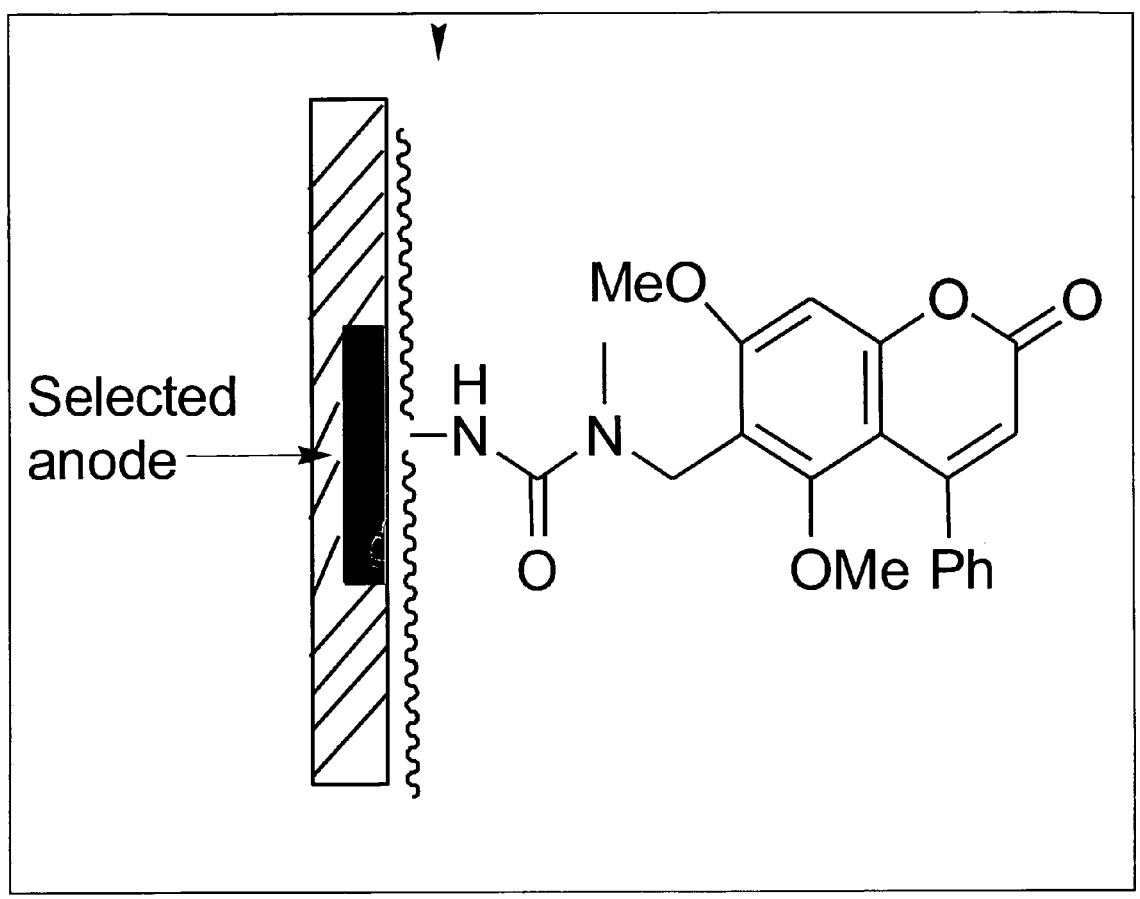
FIG. 4 shows a structure of a coumarin-tagged electrode surface.

The CV experiment was initiated by the application of a voltage followed by measurement of the resulting current. The voltage was swept from a low potential to high potential then reversed and the resulting current at each voltage step was collected. If a layer of material is on the surface of the electrode both diffusion and electron transfer of the ferrocene acetic acid/ferrocinium acetic acid cation redox couple was affected. These effects are shown in the CV data illustrated in FIG. 4. There was a large change in the both the signal intensity and charging current with the addition of antibodies specific for coumarin when compared to BSA or non-specific antibodies. The result was a 4 nA decrease in signal intensity when anti-coumarin antibodies were exposed to the electrode surface. This result highlights the extent CV was sensitive to layers of material on the electrode surface and that CV can be used as a generic tool to investigate a multitude of molecules at electrode surfaces.

Figure 8:
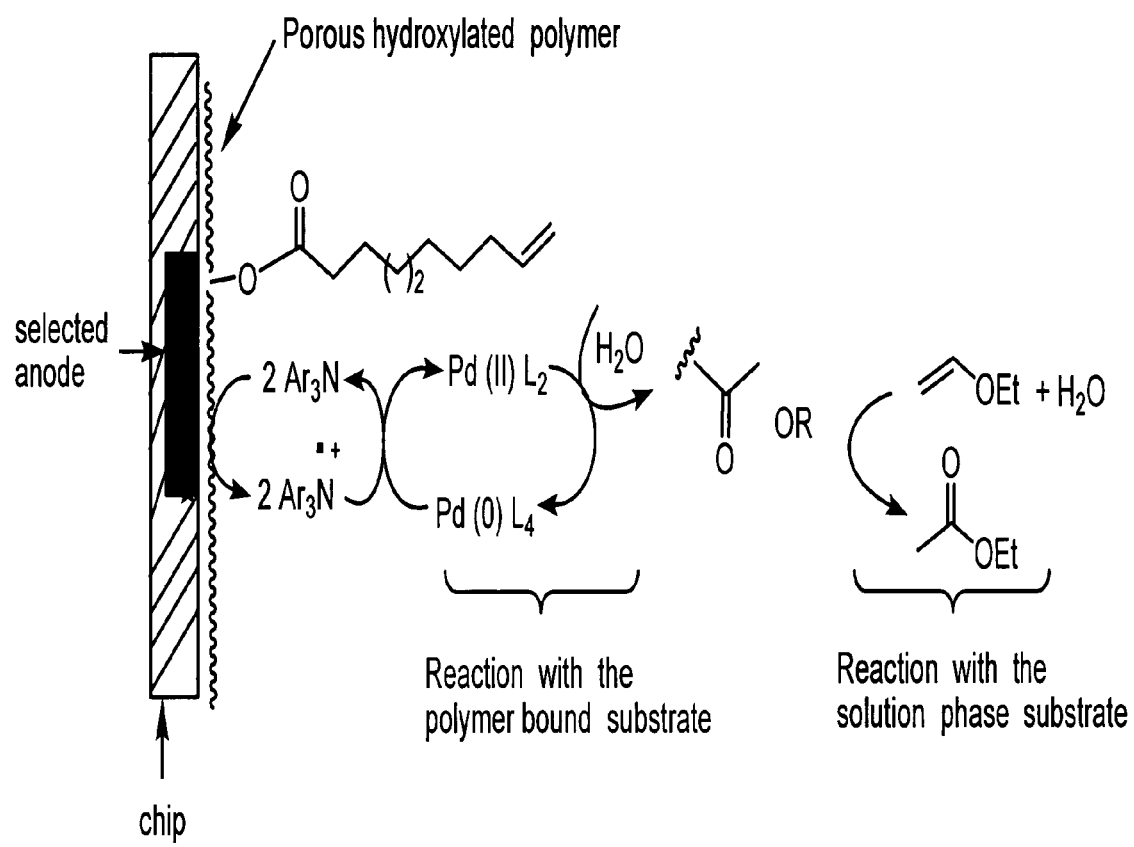
FIG. 8 shows a synthetic scheme on a selected anode (electrode) used for spatially isolating a Wacker oxidation on a electrode array device. For these reactions, the required Pd(II) reagent was generated by oxidizing a Pd(0) substrate at the selected electrodes and confined with the use of ethyl vinyl ether in the reaction medium.

FIG. 8 shows cyclic voltammetry curves for couamrin synthesized electrodes using ferrocene acetic acid/ferrocinium acetic acid couple. Specifically, the electrode array device was incubated with BSA, non-specific antibody and a coumarin specific antibody.

EXAMPLE 1

This example tested the feasibility of the inventive process. In order to test the effectiveness of this approach, an electrode array device with a surface area of about 1 cm² and having 1024 individually addressable platinum electrodes, was coated with a porous hydroxylated polymer membrane, and then treated with the N-hydroxysuccinic ester of 10-undecenoic acid as outlined in FIG. 3. The substrate was concentrated on the electrode array device in the region close to the electrodes by catalyzing the reactions with an electrogenerated base ("Electrogenerated Bases." Utley and Nielsen in *Organic Electrochemistry: Fourth Edition* Lund; Hammerich Ed.; Marcel Dekker: New York, p 1227, 2001). The base was formed by using the electrodes on the electrode array device to reduce vitamin $B_{12}$ (WO00/53625). To accomplish this, the electrode array device was submerged (along with a Pt-rod counter electrode) into a tetrabutylammonium nitrate in DMF/MeOH electrolyte solution containing the vitamin $B_{12}$. Selected electrodes were poised at a potential difference of −2.4 volts versus the Pt counter electrode for 0.5 second and off for 0.1 second for 300 cycles. These conditions were selected in analogy to earlier coupling reactions using the same electrode array devices in order to ensure selectivity (longer times generate larger quantities of reagent and more chance for migration to neighboring electrodes) and complete coverage of the electrode (extra cycles). Following the coupling reaction, any free hydroxyls remaining on the surface of the electrode array device were capped by exposing the electrode array device to acetic anhydride using the same electrogenerated base conditions.

A Wacker oxidation, outlined in FIG. 2, was then performed at selected electrodes by reversing the electrode polarity and utilizing them as anodes. Electrodes not selected for the Wacker oxidation were simply turned off. For this experiment, the electrode array device and counter electrode were submerged in 2.5 mL of 0.5 M $Et_4NOTs$ in 7:1 acetonitrile/water electrolyte solution containing 32 µg of Pd(OAc)$_2$, 1.39 mg of tris-2-bromophenylamine, and 83 µL of ethyl vinyl ether. The oxidation reaction was performed by pulsing the selected electrodes for 0.5 second at +2.4 V and 0.5 second at 0 V for either 300 or 600 cycles. The selected electrodes were chosen in order to form a checkerboard pattern on the electrode array device.

Once this experiment was completed, the ketones that were generated were converted to their 2,4-DNP derivatives by treating the electrode array device with a 0.5% DNP in 2N HCl solution and the electrode array device was incubated with a 5% BSA in PBS buffer solution containing commercially available rabbit anti-2,4-dinitrophenol antibody that is conjugated to the fluorescent probe Alexa Fluor® 488 (Molecular Probes (A-11097), Eugene, Oreg.) at 1/16 antibody to buffer (Conrad et al., *Biological Procedures Online* 2:1, 2000 and Yuan et al., *Blood* 84, 632, 1994). Next, the surface of the electrode array device was washed with PBS buffer to remove excess antibody and the electrode array device was imaged with an epifluorescence microscope using a blue filter (PBS buffer was needed on the surface of the electrode array device in order to ensure a successful image). The image shown in FIG. 1 shows that the experiment worked perfectly. It appears the reaction led only to the formation of ketones at the selected electrodes as demonstrated by the checkerboard pattern of fluorescence (indicated by the bright spots) on the electrode array device. In FIG. 1, the dark spots are electrodes that were not utilized for the oxidation (the Pt electrodes block the background fluorescent originating from the electrode array device itself).

Subsequent control experiments yielded two important observations about this first experiment. First, when Pd(II) was generated at selected electrodes on an electrode array device without the olefin substrate, a faint checkerboard pattern was still observed. It appears that the acetic anhydride capping step was not completely effective and Pd(II) generated at the electrode led to oxidation of the unprotected alcohols in the polymer membrane (Muzart, *Tetrahedron* 59:5789, 2003). An additional experiment compared "side-by-side" electrodes that had associated olefin substrate and electrodes that were devoid of any olefin substrate. In this experiment, the intensity of the fluorescent spots was significantly greater for the electrodes having the olefin substrate present. This indicates that the intensity of the fluorescent spots in the initial experiment (FIG. 1) was due primarily to the initially planned Wacker oxidation.

In a second control experiment, the ethyl vinyl ether was removed from the solution over the electrode array device. In this case, the experiment led to fluorescence seen at many electrodes that were not utilized for the oxidation as well as at a variety of random sites on the surface of the electrode array device. These data show that the use of ethyl vinyl ether was required for confining the Pd(II) to the selected electrode sites on the electrode array device.

EXAMPLE 2

This example provides a general procedure for conducting reductive amination reactions on an agarose coated electrode array device. For the oxidation of agarose: 100 µL of a solution containing 3.2 mg of Pd(OAc)$_2$ and 139 mg of tris (4-bromophenyl) amine in 10 mL of 0.5 M tetraethylammonium p-tolunesulfonate, 500 µL of ethyl vinyl ether, and 1.4 mL of 0.5 M tetraethylammonium p-tolunesulfonate was placed in 1.7 mL epi-tube. The solution was vortexed for 3 minutes. An electrode array device, spin-coated with 3% agarose in DMF, was then exposed to this solution. A potential of 2.4 V vs. a Pt counter electrode was then applied to a checkerboard pattern of electrodes for 0.5 sec followed by 0.5 sec with no applied potential. Electrodes that were not selected for reaction were left off for the entire experiment. The pattern of on and off potentials was continued for 600 cycles. The electrode array device was then washed with 2 mL of ethanol, 2N HCl, and ethanol respectively.

The subsequent reductive amination reaction used Texas red hydrazide. Briefly, the electrode array device was soaked for 12 h in a 1 mL solution of methanol containing Texas red hydrazide (0.15 mM) and sodium cyanoborohydride (0.1 M). The electrode array device was then washed with excess ethanol.

The electrolysis reaction was repeated using the alternate checkboard pattern of electrodes as the active electrodes.

A subsequent reductive amination reaction was performed using sulphonated pyrene. Briefly, the electrode array device was soaked in a 1 mL methanolic solution of trisodium 8-aminopyrene-1,3,6-trisulfonate (1.5 mM) and sodium cyanoborohydride (0.1M). Again, the reductive amination reaction was conducted for 12 hours. The electrode array device was then washed with excess methanol. This step was repeated twice, and then the electrode array device imaged using a fluorescence microscope.

Figure 10:
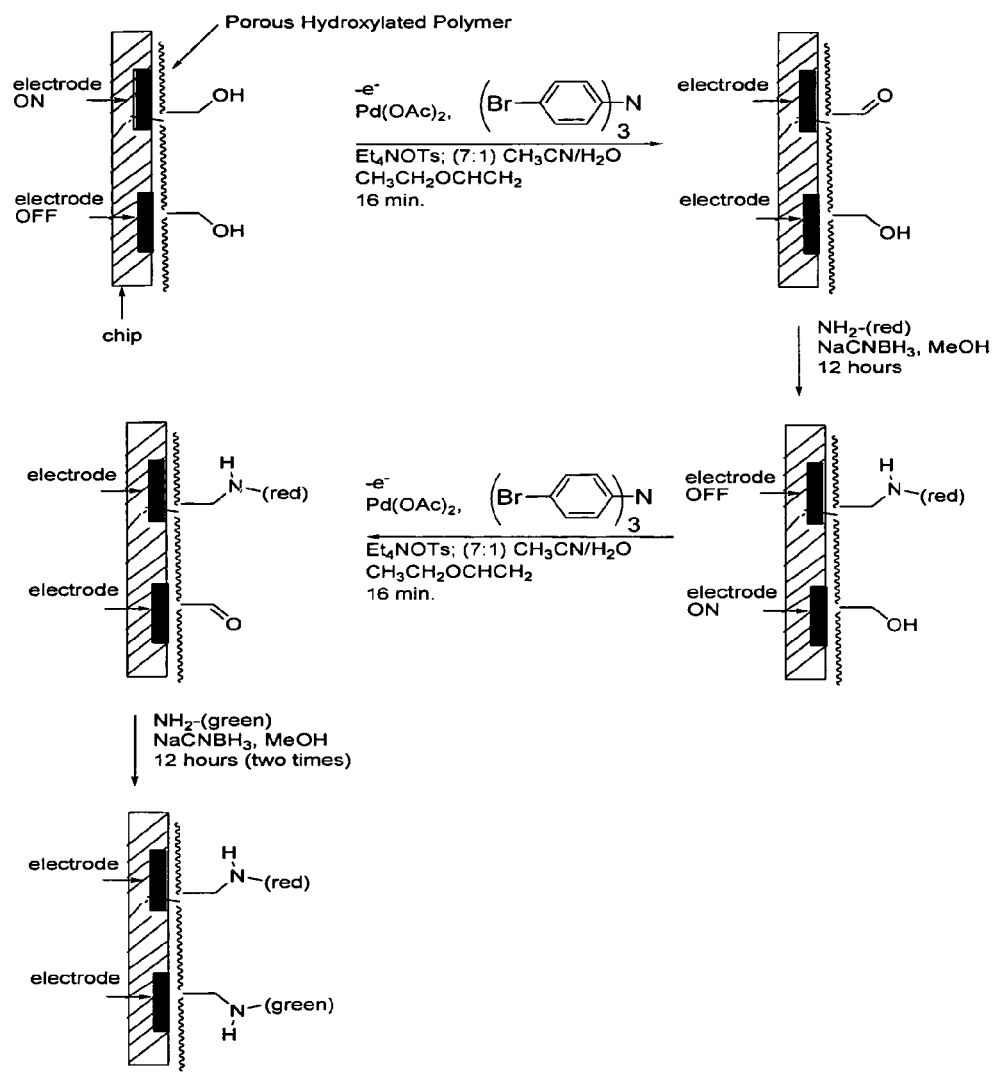
FIG. 10 shows a scheme of an experiment conducted (Example 2).

An experiment was conducted as outlined in FIG. 10 using an electrode array device containing 1024 platinum electrodes in a 1 cm² area. The initial oxidation was performed using conditions nearly identical to those used in connection with the previous Wacker oxidation (Example 1). To this end, the electrode array device was coated with a porous hydroxylated polymer and then submerged into 2.5 mL of a 0.5 M tetraethylammonium tosylate in acetonitrile/water (7:1) electrolyte solution containing 32 µg of palladium acetate, 1.39 mg of tris-4-bromophenyl amine, and 500 µL of ethyl vinyl ether. The counter electrode (cathode) for the reaction was a platinum wire that was also inserted into the reaction solution. Oxidation of the Pd(0) substrate (formed by premixing the Pd(OAc)$_2$ and ethyl vinyl ether) was performed by cycling selected electrodes in a checkerboard pattern between a potential of +2.4 V for 0.5 seconds and 0 V for 0.5 seconds. The reaction was continued for 1000 cycles. The electrode array device was then removed from the solution, washed with water and acetonitrile and then inserted into a methanol solution containing the Texas red hydrazine (red) and sodium cyanoborohydride for a period of 12 h.

Figure 11:
FIG. 11 shows an electrode array device fluorescent image from an experiment described in Example 2.

After completion of this first step, the electrode array device was imaged using a fluorescent microscope. The imaged obtained is shown in FIG. 11. Clearly, the ethylvinyl ether worked well to confine the alcohol oxidation to the desired electrodes. As can be seen in the image, no apparent "leakage" of the Pd(II) away from the selected electrodes occurred. This was especially striking since unlike previous reactions that utilized deposited substrates proximal to the electrodes, the alcohol oxidation utilized the polymer coating the entire chip as a substrate. Hence, oxidation in between the electrodes was possible. However, the confining agent appeared efficient enough to stop even this level of migration.

Figure 12:
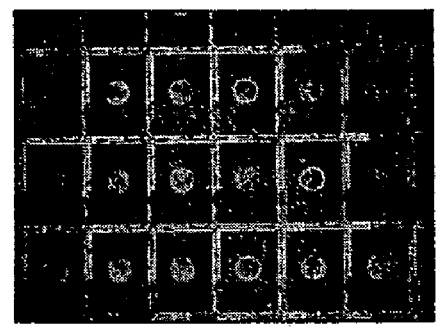
FIG. 12 shows an electrode array device fluorescent image from an experiment described in Example 2.

Having established the potential for the reductive amination using a very reactive hydrazine substrate, attention was turned toward a reaction using a less reactive aryl amine substrate (green, Shannon et al., *J. Comb. Chem.* 5:860, 2003)). The procedure was repeated exactly as outlined above in this example. However, this time, an opposite set of alternating electrodes was selected. Initially, only a faint appearance of the green fluorescence was observed. However, when the reductive amination reaction was repeated a second time the electrode array device showed the presence of the second amine, (green fluorescence/FIG. 12). Once again, confinement of oxidation and the subsequent reductive amination reaction appeared very well. None of the green fluorescent amine appeared at either unwanted electrodes or the regions in between the electrodes.

EXAMPLE 3

Figure 13A:
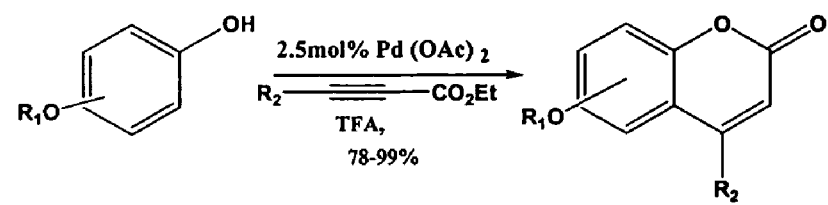
FIG. 13A shows Pd(II) catalyzed alkoxy coumarin synthesis.

This example illustrates a catalytic electrode based cycloaddition, where an electrochemical process was used to convert catalytic Pd(II) into a non-catalytic reagent and performed site selectively on an electrode array device. In this experiment Pd(II) reagent was confined to the pre-selected electrode by putting ethyl vinyl ether in the solution above the electrode array device. In order to study the generality of these reactions and the extension of the approach to a Pd(II) catalytic reaction, a site selective Pd(II) catalyzed alkoxy-Coumarin synthesis was developed. Reaction of alkoxyphenols and alkyonates in the presence of a catalytic amount of Pd(OAc)$_2$ in trifluoroacetic acid at room temperature was reported to give Coumarin derivatives in high yields. (FIG. 13A)

Figure 13B:
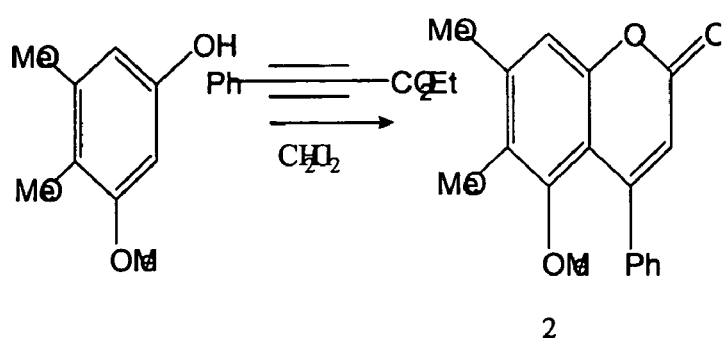
FIG. 13B shows another coumarin synthesis scheme.
Figure 13C:
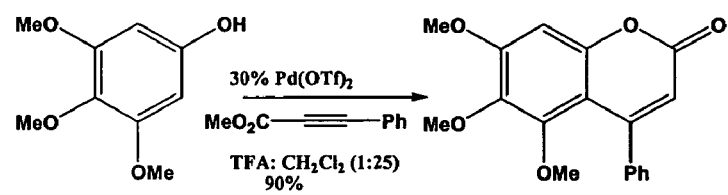
FIG. 13C shows a modified reaction condition for Pd(II) catalyzed alkoxy coumarin synthesis to fit the environment of an electrode array device.

Although the reaction gave a high yields the reactions conditions were modified in order to fit the electrode array device environment. The primary problem was that trifluoroacetic acid digests the agarose (hydroxylated porous matrix) coat on the electrode array device. After screening different reaction conditions the use of 30 mol % Pd(OTf)$_2$ as catalyst in 5% TFA in dichloromethane gave acceptable yields. (FIG. 13B). Table 1 below shows the results of various reaction conditions. The optimal reaction scheme is shown in FIG. 13C.

| Entry | TFA | Pd(OAc)$_2$, Pd(OTf)$_2$ | NaOAc | Yield |
|---|---|---|---|---|
| 1 | 2 mmol | 10 mol % Pd(OAc)$_2$ | 0 | ~20% |
| 2 | 0 | 10-30 mol % Pd(OTf)$_2$ | 0 | 0% |
| 3 | 0 | 30 mol % Pd(OTf)$_2$ | 30 mol % | 0% |
| 4 | 1 mmol | 10 mol % Pd(OTf)$_2$ | 10 mol | ~20% |
| 5 | 1 mmol | 10 mol % Pd(OTf)$_2$ | 0 | 66% |
| 6 | 4% (1:25) TFA:CH$_2$Cl$_2$ | 30 mol % Pd(OTf)$_2$ | 0 | >90% |

EXAMPLE 4

Figure 14:
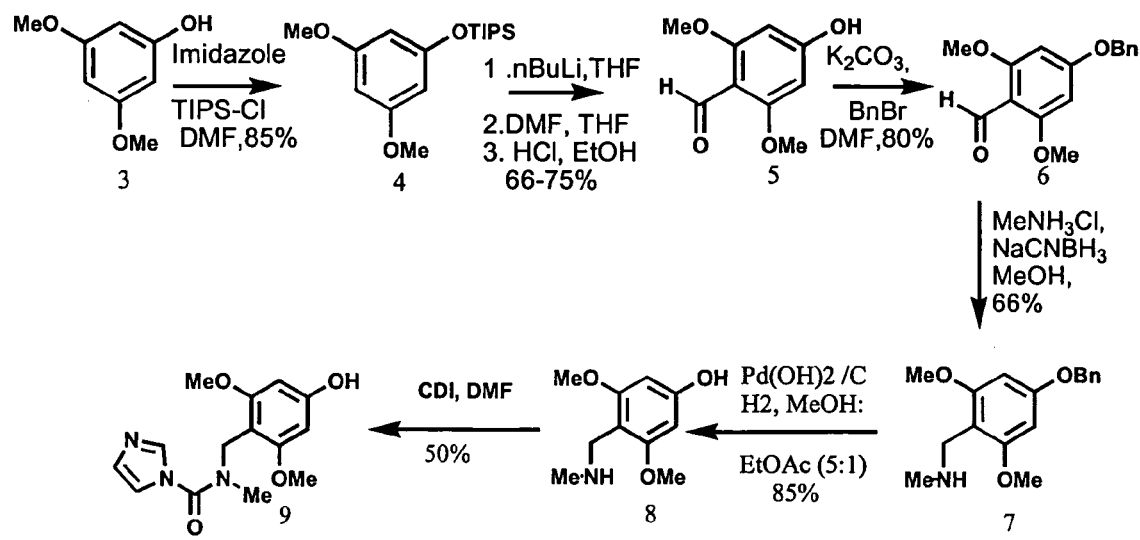
FIG. 14 shows a scheme for the synthesis of a phenol amine substrate.

This example illustrates synthesis of a solid phase substrate. In order to study the feasibility of this reaction on the electrode array device, an alkoxy phenol substrate with activated site to be coupled with the electrode array device was designed. The synthesis of phenol amine is shown in the scheme of FIG. 14.

Figure 15A:
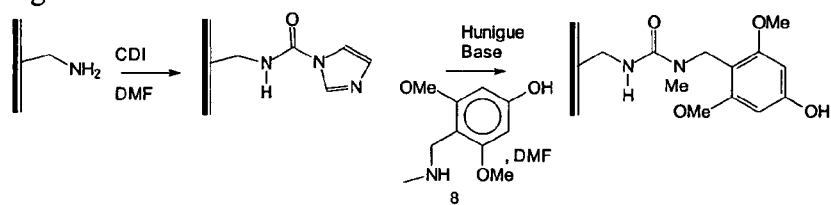
FIG. 15A shows the coupling of amine on amine based polymer using carboxyldiimadazole.
Figure 15B:
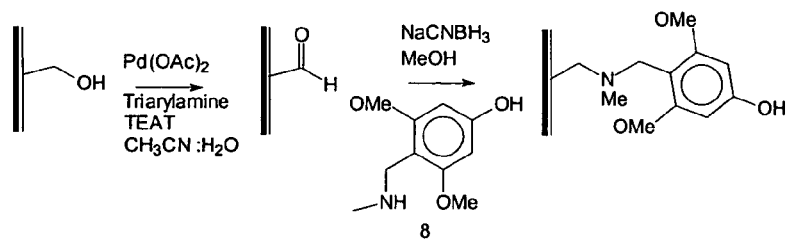
FIG. 15B shows coupling the amine of the electrode array device using reductive amination.
Figure 16:
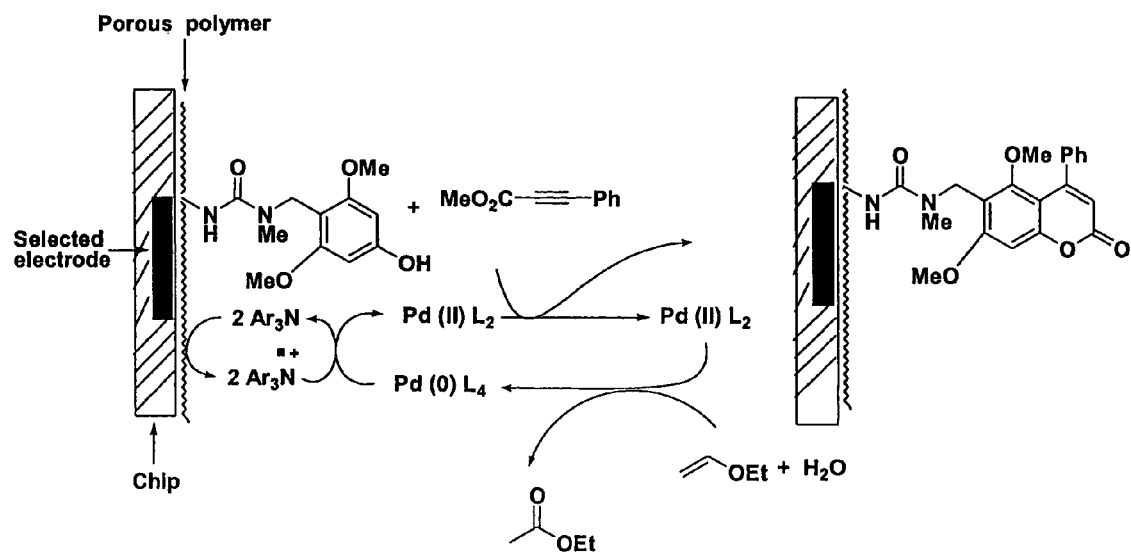
FIG. 16 shows confinement of Pd(II) catalyzed alkoxycoumarin reaction on a electrode array device.
Figure 17:
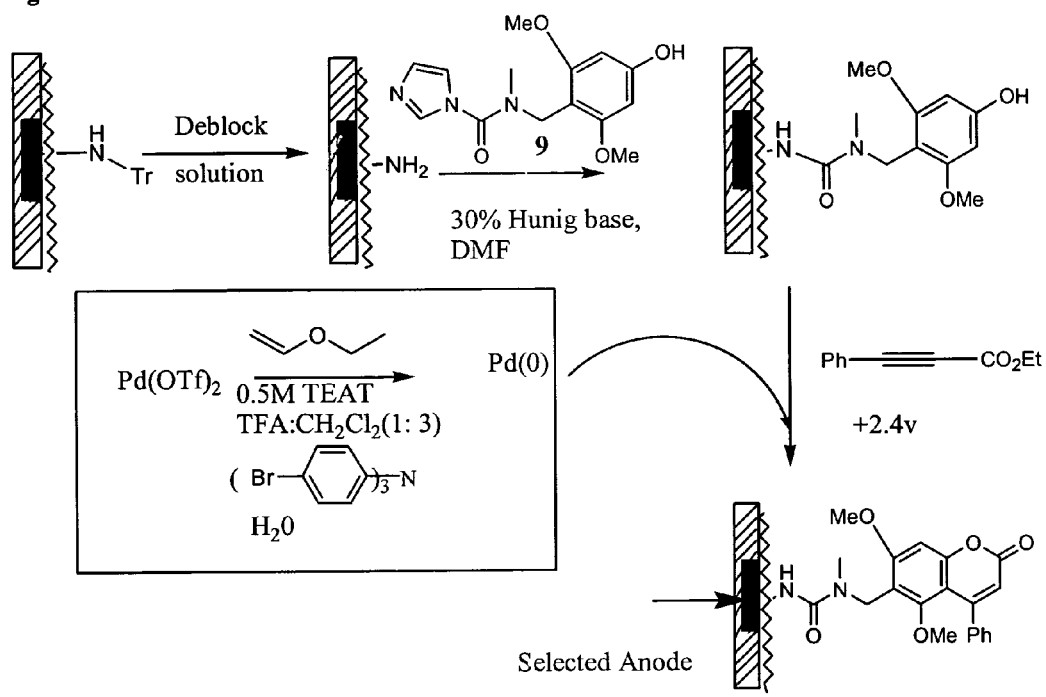
FIG. 17 shows a scheme of the synthesis of coumarin on an amine-based electrode array device.

The phenol substrate was attached onto the electrode array device. Briefly, depending on the polymer coating used on the electrode array device two methods were used to couple the alkoxy phenol on to the electrode array device. First, an amine based polymer was used, specifically, phenol amine substrate was coupled to the electrode array device by using carboxydiimidazole as a coupling agent as shown on scheme of FIG. 15A. Secondly, an agarose polymer polymer was used. Specifically, the alcohols on the agarose were oxidized electrochemically by using Wacker oxidation reaction conditions. The amine was coupled into it by using reductive amination procedure using sodium cyanoborohydride. (Scheme in FIG. 15B).

EXAMPLE 5

This example illustrates Pd(II) catalyzed coumarin synthesis on the electrode array device. This reaction utilizes the environment of the electrode array device to convert a catalytic process into stochiometric one so that it can be isolated to specific locations. Using ethyl vinyl ether undergoing Wacker oxidation with Pd(II) species on the electrode array device consumed Pd(II) reagent. The Pd(0) was reoxidized at selected sites on the electrode array device so that Pd(II) catalyzed coumarin synthesis is performed (Scheme in FIG.

16). The presence of the expected product was analyzed by using immunological assay using biotinylated anticoumarin

EXAMPLE 6

This example provides the synthesis of 4-phenyl-5,6,7-trimethoxy coumarin (2). (Scheme of FIG. 13C). A mixture of 46.3 mg of 3,4,5 tri-methoxy phenol (0.25 mmol, 1 eq.), 52.2 mg of ethyl phenyl propiolate (0.3 mmol, 1.2 eq), 24.9 mg palladium triflate (0.075 mmol, 0.3 eq.), 20 µL trifluoracetic acid in 0.5 mL dichloromethane was stirred at room temperature for 12 hours under argon gas. Then the reaction mixture was diluted with dichloromethane, washed using 5% sodium bicarbonate, water and brine. The organic layer was dried using anhydrous Mg $(SO_4)_2$ and was concentrated in vaccu to give 80 mg of a crude brown solid. The crude NMR shows the desired product as a major product and some impurities. The crude brown solid was dissolved in hexane, and recrystallized. 15 mg of pure product was isolated. However, $^1$H-NMR confirmed that the aliquot still contains the product. $H^1$NMR (300 MHz, $CD_3Cl$): δ=7.25-7.45 (m, 5H), 6.70 (S, 1H), 6.05 (S, 1H), 3.93 (S, 1H), 3.75 (S, 3H), 3.25 (S, 3H).

The synthesis of N-(2,6-dimethoxy-4-hydroxy) benzyl N-methyl amine (8) and N-carboxy imidazola-N-(2,6-dimethoxy-4-hydroxy) benzyl N-methyl amine (9)(Scheme from FIG. 14) was performed. Briefly, 4-formyl-3,5-dimethoxyphenol (5) was prepared from 3,5-dimethoxy phenol (3) following by a procedure reported by Landi and Ramig, *Synthetic Communication* 21:167-171, 1991. 3 g of 4-formyl-3,5-dimethoxyphenol (16.4 mmol, 1 eq.) and 3.4 g of potassium carbonate (24.6 mmol, 3 eq.) were placed in flame-dried 100 mL round bottom flask under argon gas. Then 55 mL of anhydrous DMF (0.3M) and 4.1 mL benzyl bromide were syringed into the reaction mixture, respectively. It was left to stir for 21 h and the reaction mixture was filtered to remove undissolved potassium carbonate. Adding 30 mL water to the solution quenched the reaction. It was extracted with 20 mL of ethyl acetate four times. The organic layer was collected and was extracted with 40 mL brine, dried with anhydrous Mg $(SO_4)_2$ and was concentrated in vaccu to give 12 g of crude product. The crude product was then chromatographed using 350 g of silica gel and gradient solvents of 25% ethyl acetate in hexane to 100% hexane. 3.6 g of the desired product (O-benzyl 4-formyl-3,5-dimethoxyphenyl ether, substrate 6) was isolated. $H^1$NMR (300 MHz, $CD_3Cl$): δ=10.3(S, 1H), 7.4 (S, 5H), 6.1 (S, 2H), 5.1 (2H, S), 3.8 (S, 6H).

A 100 mL round bottom flask was charged with 3.6 g of O-benzyl 4-formyl-3,5-dimethoxyphenyl ether (13 mmol, 1 eq), 4.4 g methylamine hydrochloride (65 mmol, 5 eq), 0.9 g Sodium cyanoborohydride (14.3 mmol, 1.1 eq) and 60 mL of anhydrous methanol. The reaction was stirred for 48 h at room temperature under argon gas. Drops of concentrated hydrochloric acid was added to it until a white cloudy gas stops evolving. Then the crude was concentrated under vacuum. 35 mL of water was added and placed into the concentrated crude and was extracted using 70 mL of ethyl acetate four times. The organic layer was dried with anhydrous Mg $(SO_4)_2$ and was concentrated in vacuo to give 2.9 g of pure product 7. $H^1$NMR (300 MHz, $CD_3Cl$): δ=9.12 (b, 1H), 7.33-7.44 (m, 5H), 6.19(S, 2H), 5.05(S, 2H), 4.15 (2H, S), 3.83 (S, 6H), 2.48(S, 3H).

A 100 mL round bottom flask was charged with 2.4 g of 7 (7.1 mmol, 1 eq), 355 mg of $Pd(OH)_2/C$ and 132 mL of 1:5 ethyl acetate: methanol. The solution mixture was bubbled with Argon gas for 1 h to deoxygenate the solvent. Then a balloon of hydrogen gas was put over the surface. The solution was stirred at room temperature for 20 h and was filtered to remove the catalyst. Then the solution was concentrated in vaccuo to give 1.2 g of product (substrate 8). $H^1$NMR (300 MHz, $CD_3OD$): δ=6.16(S, 2H), 4.12 (2H, S), 3.84 (S, 6H), 2.61 (S, 3H).

267 mg of carboxydiimidazole was dissolved in 1.5 mL DMF under argon gas in 25 mL round bottom flask. 3 mL DMF solution of 300 mg of substrate 8 was cannulated into it. It was then stirred for 17 h at room temperature. The reaction was quenched using 2 mL of brine. Next, it was extracted with ether five times. It was then dried and was concentrated in vacuo to give 210 mg of product (9). $H^1$NMR (300 MHz, $CD_3Cl$): δ=8.3(S, 1H), 7.6 (S, 1H), 7.1 (S, 1H), 6.5 (S, 2H), 3.9 (2H, S), 3.8 (S, 6H), 2.1(S, 3H).

EXAMPLE 7

For a deprotection step, an amine based electrode array device was inserted in a chamber. 0.5 mL deblock solution (trichloroacetic acid in dichlormethane solution) was syringed into the chamber and it was let to stand for 30 min. Then the deblock solution was pushed out and the electrode array device was washed by syringing in and by pushing out 1 mL DMF, 5 mL air, 1 mL $CH_2Cl_2$, 5 mL air and 30% Hünig's base in DMF, respectively.

A coupling step provided 0.5 mL of a DMF solution of N-carboxy imidazola-N-(2,6-dimethoxy-4-hydroxy) benzyl N-methyl amine (20 mg, 9) and Hünig's base (30%) was injected in the chamber with the deprotected electrode array device and was let to stand there for 30 min. Then the coupling solution was pushed out and the electrode array device was washed by syringing in and by pushing out 1 mL DMF, 5 mL air, 1 mL $CH_2Cl_2$, 5 mL air and 30% Hünig's base in DMF, respectively. This coupling step was repeated 3 times.

A capping step provided that any uncoupled amine was capped by using 30% acetic anhydride in pyridine solution. It was let to stand for 30 min.

A Pd(II) based reaction was performed using $Pd(OTf)_2$ (50 mg, 0.15 mmol) tri-bromo aryl amine (139 mg, 0.3 mmol) dissolved in 0.5 mL of 0.5M tetra ethyl ammonium tosylate in 25% $TFA/CH_2Cl_2$ in an eppendorf tube. 25 µL water and 25 µL (1.5 times the Pd concentration) ethyl vinyl ether was added into the tube and was vortexed. The tube was let to stand for 5 min. 100 µL ethyl phenyl propiolate was added into the tube. Then the solution was syringed into the chamber hooked with tested electrode array device #4754 (reference number). Then +2.4 V was passed on the electrodes of the electrode array device in a zigzag pattern for 2000 cycles of 0.5 s on and 0.5 s off pulsing. Total time was 33.3 min.

Blocking: The electrode array device was incubated in 0.2% acylated BSA in PBS for 30 minutes to block nonspecific binding of an antibody. Then the electrode array device was washed with excess PBS.

Antibody Incubating: The electrode array device was incubated in 1/100 biotinylated anti-coumarin in PBS for 30 minutes. Then it was washed with excess 2*PBS and the electrode array device was soaked in 2*PBS for 15 minutes.

Streptoavidin immobilization: The electrode array device was incubated in 1/500 Texas red conjugated streptoavidin in PBS for 30 min. Then the electrode array device was washed using excess PBS.

Figure 18:
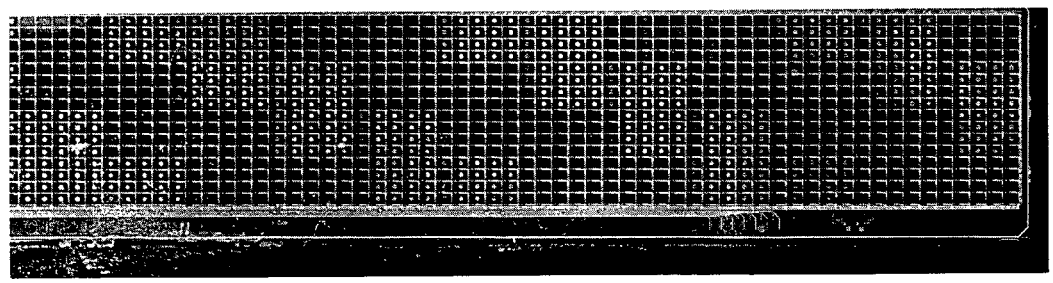
FIG. 18 shows an image under epi fluorescent microscope of the electrode array device synthesized in Example 7.

The electrode array device was scanned under Epi-fluorescence microscope (see FIG. 18).

EXAMPLE 8

Figure 19:
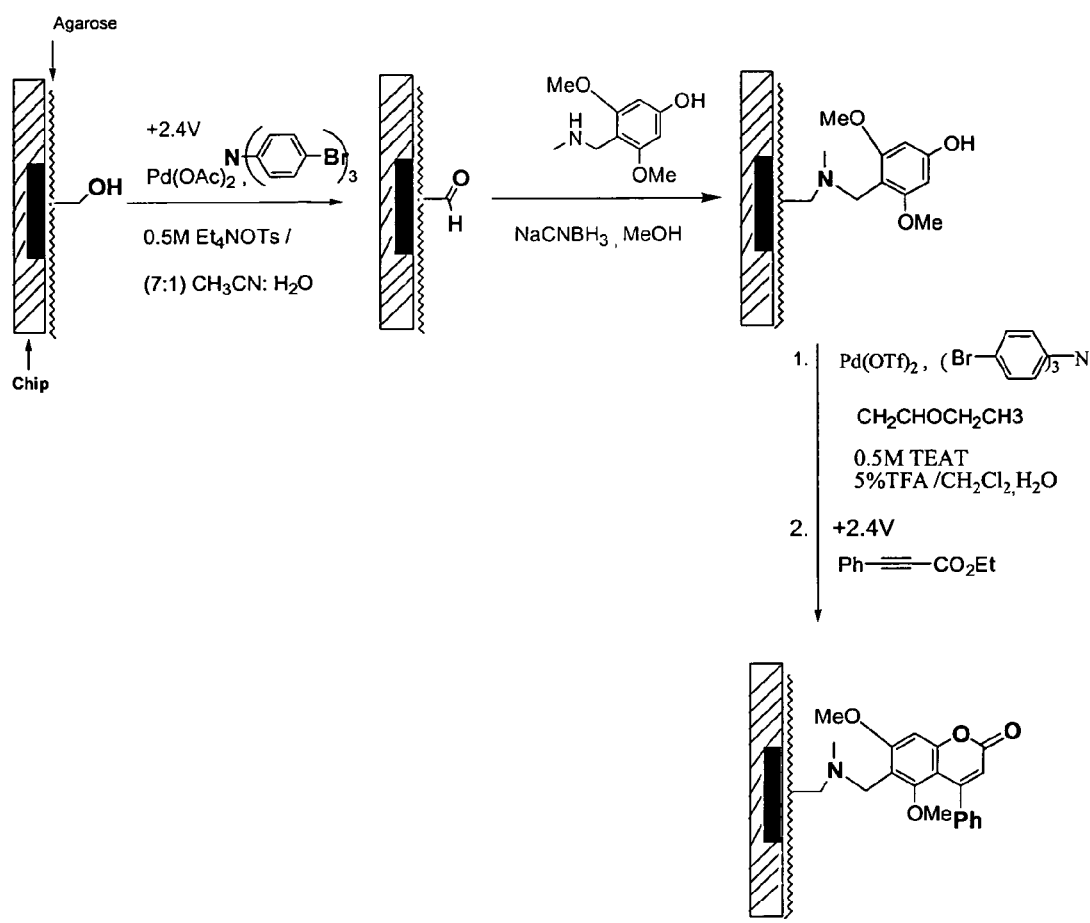
FIG. 19 shows a reaction scheme for the synthesis of coumarin on an electrode array device coated with agarose.

This example illustrates the synthesis of coumarin on an electrode array device coated with agarose. The design of this experiment is shown on the scheme of FIG. 19. The agarose was first oxidized. 300 µL of solution containing 3.2 mg Pd(OAc) 2,139 mg tris (4-bromophenyl) amine in 10 mL of 0.5M tetraethylammonium p-tolunesulfonate and 1.4 mL of 0.5M tetraethylammonium p-tolunesulfonate was placed in 1.7 mL ependorf-tube and was vortexed for one min. An electrode array device was coated with 4% agarose in DMF and then exposed to this solution. All electrodes were put on at +2.4V verses Pt electrode using 0.5 s on and 0.5 s off pulse system for 600 cycles. The electrode array device was then washed with 2 mL of ethanol, 2N HCl and ethanol respectively.

An aminomethyl phenol was used for coupling of the phenol using reductive amination. The electrode array device was soaked in 1 mL methanol solution of 0.2M of substrate 8 and 0.1 M sodium cyanoborohydride for 12 h. It was then washed with excess ethanol.

Pd(II) catalyzed alkoxy-coumarin synthesis was performed on the electrode array device. Specifically, 9.8 µg Pd(OTf)$_2$ (0.3 ηmol, 1 eq), 2.89 mg tribromoaryl amine (6 ηmol, 20 eq) dissolved in 1 mL 0.5M tetraethylammonium tosylate in 5% TFA in dichloromethane was placed in a 1.6 mL epindorf tube. 300 µL ethyl vinyl ether (3 mmol, $10^6$ eq) and 100 µL water was pipetted into the solution. The epindorf tube was vortexed for 3 min and 100 µL ethyl phenyl propiolate was pipetted. The chip docketed on echem machine is submergend in this solution. Selected electrodes were put on at +2.4 V potential with a pulse of 0.5 on and 0.5 off for 250 or 500 cycles. Then the electrode array device was dipped into 2 mL of ethanol, water, and ethanol respectively.

The electrode array device was incubated in 5% BSA in PBS for 30 min to block nonspecific binding of the antibody. Then the electrode array device was washed with excess PBS.

Figure 20:
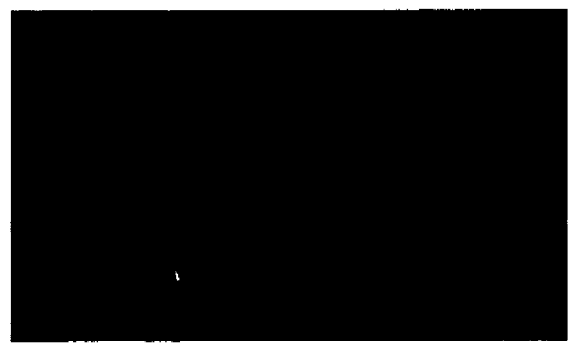
FIG. 20 shows an image of the electrode array device synthesized in Example 8.

The electrode array device was incubated in 1/100 biotinylated anti-coumarin in PBS for 30 minutes. Then the electrode array device was washed with excess 2*PBS and the electrode array device was soaked in 2*PBS for 15 min. The electrode array device was incubated in 1/500 Texas red conjugated streptoavidin in PBS for 30 min. Then the electrode array device was washed using excess PBS. The electrode array device was scanned under epi-fluorescence microscope (see FIG. 20).

We claim:

1. A process for synthesizing site-selective coumarins at known locations of an electrode array device, comprising:
   (a) providing an electrode array device with a coating of the region above the electrodes with a porous polymer matrix having free amine groups;
   (b) coupling a substituted phenol substrate at selected electrodes of the electrode array device, wherein the substituted phenol substrate is selected from the group consisting of 2-,3-,4-, or 5-substituted amino-phenols, and combinations thereof, wherein the substitution is selected from the group consisting of $C_{1-6}$ alkyl, $C_{1-6}$ alkoxy, Cl, F, Br, hydroxy, amino$C_{1-6}$ alkyl, and amino; and
   (c) performing a site selected Pd(II) catalysed cycloaddition reaction between the phenol substrate and an acetylene at selected electrode sites by providing a solution bathing the electrode array device, wherein the solution comprises a transition metal species and a confining agent, and biasing one or a plurality of selected electrodes on the electrode array device with a voltage or current to regenerate the transition metal species consumed during the cyclooxidation reaction.

2. The process for synthesizing site-selective coumarins at known locations of an electrode array device of claim 1 wherein the porous polymer matrix having free amine groups is selected from the group consisting of amidited agarose, sucrose having oligonucleotide moieties each having an amino-modifier, and combinations thereof.

3. The process for synthesizing site-selective coumarins at known locations of an electrode array device of claim 2 wherein the amino modifier is selected from the group consisting of 5'-3-aminopropyloxy, 2-aminoethoxy, 2(2-aminoethoxy) ethoxy, 2(2(2aminoethoxy)ethoxy)ethoxy, 6-amino, and combinations thereof.

4. A process for site-selective oxidation of alcohols on an electrode array device, comprising:
   (a) providing an electrode array device with a coating of at least the region above the electrodes with a porous polyhydroxylated polymer matrix;
   (b) performing a site selected oxidation reaction at selected electrode sites by providing a solution bathing the electrode array device, wherein the solution comprises a transition metal species; and
   (c) coupling an amine substrate at selected electrodes of the electrode array device to form a bound substrate.

5. The process for site-selective oxidation of alcohols on an electrode array device of claim 4 wherein the oxidation reaction further comprises biasing one or a plurality of selected electrodes on the electrode array device with a voltage or current to regenerate the transition metal species consumed during the oxidation reaction.

6. The process for site-selective oxidation of alcohols on an electrode array device of claim 4 wherein the porous polyhydroxylated polymer matrix is composed of a material selected from the group consisting of agarose, destrose, PEG, dextran, polyvinylalcohol, porous crosslinked polystyrene, poly(2 hydroxyethylacrylate), poly(hydroxylpropylacrylate), and combinations thereof.

* * * * *